United States Patent [19]

Sellstedt et al.

[11] 4,160,100

[45] Jul. 3, 1979

[54] OXAMIC ACID DERIVATIVES

[75] Inventors: John H. Sellstedt, Pottstown; Charles J. Guinosso, King of Prussia, both of Pa.; Albert J. Begany, Tucson, Ariz.

[73] Assignee: American Home Products Corporation, New York, N.Y.

[21] Appl. No.: 669,567

[22] Filed: Mar. 23, 1976

Related U.S. Application Data

[63] Continuation-in-part of Ser. No. 542,465, Jan. 20, 1975, Pat. No. 3,966,965, which is a continuation-in-part of Ser. No. 344,466, Mar. 23, 1973, abandoned.

[51] Int. Cl.² .............................................. C07C 101/54
[52] U.S. Cl. ...................................................... 560/43
[58] Field of Search .................................. 260/471 A

[56] References Cited

U.S. PATENT DOCUMENTS

| | | | |
|---|---|---|---|
| 3,317,584 | 5/1967 | Stoffel | 260/465 |
| 3,511,804 | 5/1970 | Duennenberger et al. | 260/45.85 |

OTHER PUBLICATIONS

Baker, B. R. and P. Almaula, J. Org. Chem. 27, 4672, (1962).
Edmond, J. D. et al., Br. J. Pharmac. Chemother., (1966), 27, 415-426.
Tierie, G., Rec. Trav. Chim. 52, 420-424 (1933).
Baruffinil, A. et al., Il Farmaco, Ed. Sci., vol. XXII, pp. 718-734.

*Primary Examiner*—Donald G. Daus
*Assistant Examiner*—Lisa Jones
*Attorney, Agent, or Firm*—Richard K. Jackson

[57] ABSTRACT

Anti-allergic agents of aromatic and heterocyclic oxamic acid derivation present the following formula:

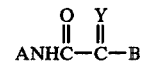

in which

A is a member selected from the group consisting of 2-thiazolyl, 2-pyridyl, 2-pyridyl-N-oxide, 6-(lower)alkyl-2-pyridyl, 3-cyano-2-pyridyl, 3-pyridyl, 4-pyridyl, 2-pyrimidinyl, 2-pyrazinyl, α-naphthyl, β-naphthyl, phenyl, 2,6-di-chlorophenyl, and substituted phenyl moieties containing from one to three substituents in any of the 2,3,4 and 5 positions of the phenyl ring, independently selected from the group consisting of lower alkyl, lower alkylthio, lower alkylsulfinyl, lower alkoxy, hydroxy(lower)alkoxy, 2-(lower alkoxy oxalyloxy) ethoxy, benzyloxy, N-mono-and di-lower alkylamino(lower)alkoxy, halo, sulfamyl, polyhalo(lower)alkyl, carbamyl, N-lower alkylcarbamyl, nitro, mono-and di-lower alkylamino, phenylazo, carboxy, lower alkylcarbonyl, cyano, carb(lower)alkoxy, phenoxy(lower)alkoxy, lower alkoxyoxalamido and lower alkoxyoxalamidophenoxy radicals;

B, when taken alone, is a member selected from the group consisting of —OH, lower alkoxy, —NH₂, —NHOH, cyclohexyloxy and phenoxy; and Y is a member selected from the group consisting of oxygen and when taken with B and the carbon atom to which they are attached, forms the moiety

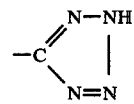

31 Claims, No Drawings

OXAMIC ACID DERIVATIVES

RELATED APPLICATIONS

This application is a continuation-in-part of Ser. No. 542,465, filed Jan. 20, 1975, now U.S. Pat. No. 3,966,965, which is a continuation-in-part of Ser. No. 344,466 filed Mar. 23, 1973, now abandoned.

BACKGROUND OF THE INVENTION

Atopic immediate sensitivity is the chief manifestation found in animals suffering from bronchial asthma, seasonal pollinosis (e.g. hay fever), allergic rhinitis, urticaria, allergic conjunctivitis, food allergies and anaphylactoid reactions. The substances most frequently responsible for clinically manifest sensitivities are plant pollen, animal feathers and danders, dust, milk and wheat, whether inhaled or ingested.

Atopic hypersensitivity is found in man, dog and other animals. Its occurrance is exceptionally found in the lower animals.

The presence of antibodies associated with atopic hypersensitivity reactions in the host serum is established by the passive sensitization of the skin of a normal recipient, after injection of serum from a sensitized host into a skin site followed by injection of antigen into the same area 24 hours later, resulting in a local hive. This is commonly referred to as the Prausnitz-Kustner (P-K) reaction.

The antibody associated with atopic hypersensitivity possesses distinctive features in that it does not in all forms precipitate with its antigen, fails to pass the placenta from mother to fetus, has special affinity for the skin, frequently lacks specificity toward an individual antigenic factor and is usually labile at about 56° C. after two hours.

The homocytotropic antibody found in or induced in the rat is related in function and reaction to immunoglobulin E (reagin or IgE) found in the human. The correlation between homocytotropic antibody in the rat and IgE in the human has been established through the common effects obtained from chemical reactions, immunological reactions and drug responses in the two species hosting those antibodies. In the human, reagin is the antibody responsible for atopic immediate hypersensitive reactions. In the rat, the homocytotropic antibody is responsible for atopic immediate hypersensitive reactions.

In theory, reagin, influences the cell membrane of a mast cell by reacting with an antigen, to initiate the reaction(s) within the mast cell which ultimately releases a mediator such as Bradykinin, SRS-A (slow reacting substance-A), histamine and other unknown substances. The mediator effects a change in surrounding cell wall permeability permitting a rapid change in flow or exudance of mediator(s) from the cells, resulting in an allergic attack symptom. The various methods commonly employed to relieve the symptoms of allergic attack, none of which are considered to be quite acceptable, are to (1) avoid attack by the antigen, (2) block the production of antibody with an immunosuppressant, (3) block the action of the mediators on the cell under attack by administration of anti-histaminics, anti-5-hydroxy-tryptamines (5-HT) or anti-inflammatories, or (4) stimulate the cell under attack to negate the action of the mediator through the action of bronchodilators such as Isoprel ® or a Xanthine.

The only compound known to date to operate as an antiallergic by blocking reaction(s) within the mast cells, thereby preventing the production and release of mediators, is disodium cromoglycate. (INTAL ®).

Derivatives of oxamic acids have been employed in the past as intermediates for polymer formation and as tools for chemical research. Each of the known oxamic acid derivatives included as part of the new use aspect of this application is accompanied with a reference citation in the working examples, infra.

DESCRIPTION OF THE INVENTION

In accordance with this invention, there is provided a process for preventing the release of pharmacological mediators from an immediate hypersensitivity reaction between reaginic type antibodies and an antigen, thereby preventing the symptoms manifest in bronchial asthma, seasonal pollinosis, allergic rhinitis, urticaria, allergic conjunctivities, food allergy and anaphylactoid reactions of a sensitized animal, which comprises prophylactically administering to said animal an effective amount of a compound of the formula:

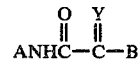

in which

A is a member selected from the group consisting of 2-thiazolyl, 2-pyridyl, 2-pyridyl-N-oxide, 3-(lower) alkyl-2-pyridyl, 6-cyano-2-pyridyl, 3-pyridyl, 4-pyridyl, 2-pyrimidinyl, 2-pyrazinyl, α-naphthyl, β-naphthyl, phenyl, 2,6-dichlorophenyl, and substituted phenyl moieties containing from one to three substituents in any of the 2,3,4 and 5 positions of the phenyl ring, independently selected from the group consisting of lower alkyl, lower alkylthio, lower alkylsulfinyl, lower alkoxy, hydroxy(lower)alkoxy, 2-(lower alkoxy oxalyloxy) ethoxy, benzyloxy, N-mono-and di-lower alkylaminoalkoxy, halo, sulfamyl, polyhalo(lower)alkyl, carbamyl, N-lower alkylcarbamyl, nitro, mono- and di-lower alkylamino phenylazo, carboxy, lower alkylcarbonyl, cyano, carb(lower)alkoxy, phenoxy(lower)alkoxy, lower alkoxyoxalamido and lower alkoxyoxalamidophenoxy radicals;

B, when taken alone, is a member selected from the group consisting of —OH, lower alkoxy, —NH$_2$, —NHOH, cyclohexyloxy and phenoxy; and Y is a member selected from the group consisting of oxygen and when taken with B and the carbon atom to which they are attached, forms the moiety

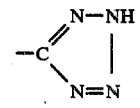

The preferred method aspect of this invention comprises administering to a sensitized animal a compound which, in minimal dosage quantity, will suppress the allergic response to a degree of or in excess of 75 percent of the characteristic wheal size of sensitized skin tissue, which compounds present the structural formula:

in which

A is a 2-thiazolyl, 2-pyridyl, 3-methyl-2-pyridyl, 2-pyridyl-N-oxide, 3-pyridyl, 4-pyridyl, 2-pyrimidinyl, 2-pyrazinyl, α-naphthyl, β-naphthyl, phenyl, 2,6-dichlorophenyl or substituted phenyl moiety containing from one to three substituents, in any of the 2,3,4 and 5 positions of the phenyl ring, independently selected from the group consisting of lower alkyl, fluoro, lower alkoxy, hydroxy(lower)alkoxy, N-mono- or di(lower)alkylamino(lower)alkoxy, (lower)alkylthio, carbamyl, carb(lower)alkoxy, 2-(lower alkoxy oxalyloxy) ethoxy, trifluoromethyl, nitro, (lower)alkoxyoxalamido and phenoxy(lower)alkoxy radicals B, when taken alone, is lower alkoxy, and Y, when taken alone, is oxygen and when taken with B and the carbon atom to which they are attached forms the moiety

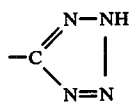

The novel aromatic and heterocyclic oxamic acid derivatives form an additional aspect of this invention.

The aromatic oxamic acid derivatives present the formula:

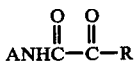

in which

R is a member selected from the group consisting of —OH, lower alkoxy, cyclohexyloxy, phenoxy, and amino radical; and A is a member selected from the group consisting of 2-cyano-phenyl, 3-fluorophenyl, 4-phenylazophenyl, 4-carbamylphenyl, 2-nitro-4-trifluoromethylphenyl, 2-cyano-3-methoxyphenyl, 4-nitro-3-trifluoromethylphenyl, 5-chloro-2-sulfamoylphenyl and

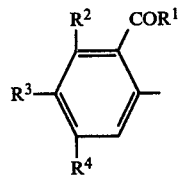

wherein $R^1$ is a member selected from the group consisting of hydroxyl, lower alkyl, lower alkoxy, lower alkylamino and amino radicals;

$R^2$ is a member selected from the group consisting of hydrogen, lower alkoxy, hydroxy(lower)alkoxy, N-mono- and di-lower alkylamino(lower)alkoxy, halo, phenoxy(lower)alkoxy, 2-(lower alkoxy oxalyloxy)ethoxy, benzyloxy, lower alkylthio, mono- and di- lower alkylamino, and lower alkyl sulfinyl, with the proviso that when $R^2$ is hydrogen, $R^1$ is other than hydroxyl or lower alkoxy;

$R^3$ is a member selected from the group consisting of hydrogen, lower alkyl, lower alkoxy, halo and nitro; and $R^4$ is a member selected from the group consisting of hydrogen, lower alkyl and lower alkoxy; with the proviso that one of $R^2$, $R^3$ and $R^4$ must be other than hydrogen.

Of the described aromatic oxamic acid derivatives, the preferred aromatic compound aspect of this invention embraces those novel compounds reducing the wheal and flare manifestation in the tissue of a sensitive animal in an amount equal to or greater than 75 percent of the allergic response. Those compounds present the following structural formula:

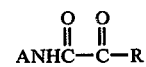

in which

R is lower alkoxy; and

A is a member selected from the group consisting of 3-fluorophenyl, 2-cyano-3-methoxyphenyl, 4-nitro-3-trifluoromethylphenyl, 5-chloro-2-sulfamoylphenyl and

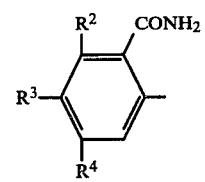

wherein $R^2$ is a member selected from the group consisting of hydrogen, lower alkoxy, di(lower)alkylamino (lower)alkoxy, hydroxy(lower)alkoxy, phenoxy(lower)alkoxy 2-(lower alkoxy oxalyloxy)ethoxy and lower alkylthio radicals;

$R^3$ is a member selected from the group consisting of hydrogen, lower alkyl, and lower alkoxy radicals;

$R^4$ is a member selected from the group consisting of —H, lower alkyl and lower alkoxy with the proviso that one of $R^2$, $R^3$ and $R^4$ must be other than hydrogen.

The novel heterocyclic oxamic acid derivatives of this invention are of the formula:

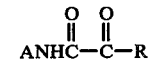

in which

A is a member selected from the group consisting of 2-pyridyl-N-oxide, 6-methyl-2-pyridyl, 3-cyano-2-pyridyl, 3-pyridyl, 4-pyridyl, 2-pyrazinyl and 2-pyrimidinyl, and R is lower alkoxy.

The term "lower" used throughout this application to modify alkyl, alkoxy, and the like, is intended to embrace univalent aliphatic hydrocarbon radicals containing from 1 to 6 carbon atoms. The term "halo" is used to embrace chlorine, bromine, iodine and fluorine.

Each of the compounds disclosed in this application has been demonstrated to relieve atopic allergic manifestations, when administered intraperitoneally to sensitized rats. Several of the compounds tested were found to be effective anti-allergy agents when administered orally to the sensitized animals.

The technique employed to establish the anti-allergic activity of the disclosed compounds is reported in Immunology, vol. 16, pp. 749-760 (1969) and involves four male Charles River rats (200-250 grams body weight) per group to provide a control, a host for administration of a standard anti-allergic compound (disodium cromoglycate) and animals for the test compound. The rats were injected intracutaneously on their shaved backs with sera from rats immunized with egg albumin and pertussis vaccine. Twenty-four hours after the initial injections, the test compound is administered intraperitoneally or orally at a dosage level of 200 milligrams per kilogram host body weight. Five minutes later one milliliter of a 0.5 percent solution of Evans blue dye and 8 milligrams of egg albumin is injected intravenously. After forty minutes, the animal is sacrificed and the bleb size on its back is measured. The mean bleb size for the animals administered the test compound is calculated and the percent inhibition is determined by comparison with the control animal. A representative number of the compounds were tested a dosage levels considerably below 200 milligrams per kilogram host body weight to establish the activity of the compounds at minimal concentrations as low as 3 milligrams per kilogram host body weight.

Although the mechanism by which the compounds of this invention function is not absolutely known, applicants have found that the compounds of this invention, in a manner believed to be similar to the function of INTAL ®, block reaction(s) in the mast cell leading to the production and release of mediators.

The compounds of this invention permit the occurrence of a non-productive antigen-antibody interaction. They effectively block the IgE type reaction and have little or no effect on the other immunoglobulins such as IgG, IgM, IgA and IgD.

The compounds of this invention have no pharmacological response pattern similar to known anti-allergics in that they have no anti-hypertensive activity (no cardiovascular effect, etc.), they have no analgesic activity, they have no central nervous system activity, they have no immunosuppressive activity, they have no activity against histamine, serotonin, Bradykinin, etc. and they have no endocrinological activity.

In sum, the compounds of this invention block the release of mediators commonly resulting from the antigenantibody reaction as exemplified in a passive cutaneous anaphylaxis test (PCA) using rat homocytotropic antibody - a known correlate of human reaginic antibody.

By analogy to disodium cromoglycate and its activity correlation between standard test animals, domestic animals and man, the compounds of this invention have been established as anti-allergic agents suitable for the same uses at analogous doses and through the same routes of administration as INTAL ®. Several of the compounds of this invention have been found to be effective anti-allergic agents when administered orally. The orally active compounds of special interest are the lower alkyl pyridyloxamates their N-oxides, lower alkyl and cyano ring substituted derivatives (methyl, ethyl and propyl 2-pyridyloxamates, ethyl 4-pyridyloxamate, ethyl 3-pyridyl-oxamate), N-(2-pyridyl)oxamic acid N'-oxide ethyl ester, (6-methyl-2-pyridyl)oxamic acid ethyl ester, (3-cyano-2-pyridyl)oxamic acid ethyl ester, the lower alkyl pyrazinyloxamates (ethyl 2-pyrazinyloxamate), methyl, ethyl and i-propyl oxanilate, 1H-tetrazole-5-carboxanilide, ethyl 3'-methyloxanilate, ethyl 4'-methoxyoxanilate, ethyl and secondary butyl 2'-carbamoyl-3'-methoxyanilate, ethyl 4'-nitro-3'-(trifluoromethyl)oxanilate and ethyl 1-naphthyloxamate, 2'-carbamoyl-3'-(2-hydroxypropoxy)oxanilic acid ethyl ester, (2-carbamoyl-3,5-dimethoxyphenyl)oxamic acid ethyl ester, oxalic acid (2-[2-aminocarbonyl-3-ethoxy carbonylcarbonylaminophenoxy]ethyl)ethyl ester, [2-carbamoyl-3(2-hydroxyethoxy)phenyl]oxamic acid ethyl ester, 3-benzyloxy-2-carbamoylphenyl)oxamic acid ethyl ester, (4-dimethylaminophenyl)oxamic acid ethyl ester, [2-(aminocarbonyl)-3-(dimethylamino)-phenyl]oxamic acid ethyl ester, [2-carbamoyl-3-(methylthio)phenyl]oxamic acid ethyl ester and [(2-aminocarbonyl-3-methylsulfinylphenyl)amino]oxo acetic acid ethyl ester.

Thus, there is provided herewith a method for suppressing allergic manifestations of atopic immediate sensitivity in warm-blooded human and non-human animals, the latter including domesticated animals such as the mouse, rat, hamster, gerbil, dog, cat, sheep, goat, horse, cow, and the like, by administering an effective amount of one or more of the compounds disclosed in this application by oral, topical, parenteral, rectal, vaginal or inhalation routes. Since the compounds of this invention afford no pharmacological response pattern similar to or antagonistic to common anti-allergics, they may be administered in conjunction with known compounds effecting anti-histaminic, anti-hypertensive, analgesic, central nervous system depressant, immunosuppressive, anti-serotonin, anti-Bradykinin or endocrinological responses. In addition, those conventional adjuvants known to the art may be combined with the anti-allergics of this invention to provide compositions and solutions for administrative purposes, although it is considered desirable and feasible to employ the anti-allergics as neat or pure compounds without additives other than for purposes of providing suitable pharmaceutical solution or liquid or vapor suspensions.

The effective dose range in test animals has been established to be from about 1.5 milligrams per kilogram to a dosage resulting in 100 percent prevention of allergic responses at 5 milligrams per kilogram host body weight upon administration intraperitoneally. The oral dose range lies from about 1.5 milligrams per kilogram to 90 percent prevention of allergic response at 200 milligrams per kilogram host body weight. As an inhalant the dose is from that of INTAL ®, (about 20 milligrams) to 1/20th that quantity administered as needed prior to attack. Thus the dosage contemplated for human use based upon the potency of the compounds administered lies from about 100 milligrams to 1 gram, preferably 250 milligrams to about 750 milligrams in unit dosage form to be administered when necessary and to the degree of the desired response, in single or plural doses under the guidance of a physician.

The compounds of this invention have not been found to be toxic to mice, the standard experimental animal in toxicity studies of this nature, at any administered dose up to and in excess of two grams per kilogram host body weight. No toxic level has been found in other standard test animals. the anti-allergic compounds of this invention appear to be free from side effects common to other anti-allergics such as sedation, dizziness, depression, etc.

The aromatic and heterocyclic oxamic acid derivatives are generally prepared by reaction of an appropriately substituted aromatic amine or heterocyclic amine with an appropriately substituted oxalylchloride in the presence of an acid acceptor, such as pyridine, at ambient temperature. The technique employed in the preparation of each of the specially disclosed compounds is presented in the following working examples either in detail or by citation of the appropriate literature, the latter being incorporated herein by reference. Throughout the following Examples, reference is made to CA (Chemical Abstracts), Zh. Obshch. Khim (The Journal of General Chemistry — Russia), Rec. Trav. Chim (Recueil des Travaux Chimique des Pays-Bas-Netherlands), Heilbron (Dictionary of Organic Compounds), Ber. Deut. Chem. (Berichte der deutschen chemischen Gosellschaft), J. Org. Chem. (Journal of Organic Chemistry), J.A.C.S. (Journal of the American Chemical Society) and Farmaco, Ed. Sci. (Il Farmaco Scientifica Edition — Italy).

In the working examples, the number following the entitled compound refers to intraperitoneal/oral activity data obtained at a dosage level of 200 milligrams per kilogram host body weight, unless otherwise indicated. The activity data represents the percent inhibition of the mean bleb size of sensitized rats administered the named compound in accordance with the test procedure presented, supra. The oral data is representatively presented for those compounds exhibiting inhibition of fifty percent or more of the weal size in the test animals at 200 milligrams per kilogram host body weight unless otherwise indicated.

EXAMPLE 1

(2-Thiazolyl)oxamic acid ethyl ester. 100

The title compound is known in the literature: C.A.: 60 (10591c). Zh. Obshch Khim., 34(1), 28–32 (1964). It is crystalized from ethanol, m.p. 174°–177° C.

EXAMPLE 2

(2-Pyridyl)oxamic acid ethyl ester. 100/95

The title compound is known in the literature: P. A. Petyunin et.al., Zh. Obshch. Khim., 32, 1395–8 (1962). It is crystallized from diethyl ether, m.p. 73°–75° C.

EXAMPLE 3

(2-Pyrimidyl)oxamic acid ethyl ester. 82

2-Aminopyrimidine (2.85 g, 0.03 mole) is condensed with 3.7 ml. (0.033 mole) of ethyl oxalyl chloride in 100 ml. dichloromethane in the presence of 4.83 ml. (0.06 mole) pyridine at 10° C. with stirring, giving 2.06 g. of the title compound, m.p. 96°–99° C., after crystallization from ethanol.

Elemental Analysis for $C_8H_9N_3O_3$: Calc'd: C, 49.23; H, 4.65; N, 21.53. Found: C, 49.05; H, 4.68; N, 21.57.

EXAMPLE 4

(4-Pyridyl)oxamic acid ethyl ester. 100/34

4-Aminopyridine (2.82 g., 0.03 mole) is condensed with 3.7 ml. (0.033 mole) of ethyl oxalyl chloride in a manner similar to example 3, giving 1.26 g. of the title compound, m.p. 110°–113° C., after crystallization from diethyl ether.

Elemental Analysis for $C_9H_{10}N_2O_3$: Calc'd: C, 55.66; H, 5.19; N, 14.43. Found: C, 55.88; H, 5.15; N, 14.64.

EXAMPLE 5

(3-Pyridyl)oxamic acid ethyl ester. 100/84

3-Aminopyridine (2.82 g., 0.03 mole) is condensed with 3.7 ml. (0.033 mole) of ethyl oxalyl chloride in a manner similar to example 3, giving 2.36 g. of the title compound, m.p. 98°–100° C., after crystallization from diethyl ether.

Elemental Analysis for $C_9H_{10}N_2O_3$: Calc'd: C, 55.66; H, 5.19; N, 14.43. Found: C, 55.40; H, 5.13; N, 14.71.

EXAMPLE 6

(2-Pyrazinyl)oxamic acid ethyl ester. 100/83

Aminopyrazine (2.88 g., 0.03 mole) is condensed with 3.7 ml. (0.033 mole) of ethyl oxalyl chloride in a manner similar to example 3, giving 3.63 g. of the title compound, m.p. 134°–137° C., after crystallization from ethanol.

Elemental analysis for $C_8H_9N_3O_3$: Calc'd: C, 49.23; H, 4.65; N, 21.53. Found: C, 48.99; H, 4.58; N, 21.56.

EXAMPLE 7

(2-Pyridyl)oxamic acid methyl ester. 77/100

2-Aminopyridine (2.82 g, 0.03 mole) is condensed with 3.04 ml. (0.033 mole) of methyl oxalyl chloride in a manner similar to example 3, giving 3.18 g of the title compound, m.p. 102°–106° C., after crystallization from diethyl ether.

Elemental Analysis for $C_8H_8N_2O_3$: Calc'd: C, 53.33; H, 4.48; N, 15.55. Found: C, 53.54; H, 4.47; N, 15.76.

EXAMPLE 8

(2-Pyridyl)oxamic acid n-propyl ester. 58/77

2-Aminopyridine (2.82 g, 0.03 mole) is condensed with 4.26 ml (0.033 mole) of n-propyl oxalyl chloride in a manner similar to example 3, giving 2.2 g of the title compound, m.p. 56°–59° C., after crystallization from diethyl ether.

Elemental Analysis for $C_{10}H_{12}N_2O_3$: Calc'd: C, 57.68; H, 5.81; N, 13.36. Found: C, 57.72; H, 5.84; N, 13.48.

EXAMPLE 9

(2-Pyridyl)oxamic acid isopropyl ester. 100

2-Aminopyridine is condensed with isopropyl oxalyl chloride in a manner similar to example 3 to afford the title compound as a liquid.

Elemental Analysis for $C_{10}H_{12}N_2O_3$: Calc'd: C, 57.68; H, 5.81; N, 13.46. Found: C, 57.15; H, 6.04; N, 13.51.

EXAMPLE 10

(2-Pyridyl)oxamic acid n-butyl ester. 100

2-Aminopyridine is condensed with n-butyl oxalyl chloride in a manner similar to example 3 to afford the title compound, m.p. 35°–37° C.

Elemental Analysis for $C_{11}H_{14}N_2O_3$: Calc'd: C, 59.45; H, 6.35; N, 12.60. Found: C, 59.16; H, 6.72; N, 12.45.

EXAMPLE 11

(2-Pyridyl)oxamic acid cyclohexyl ester. 53

2-Aminopyridine is condensed with cyclohexyl oxalyl chloride in a manner similar to example 3 to afford the title compound, m.p. 62°–64° C.

Elemental Analysis for $C_{13}H_{16}N_2O_3$: Calc'd: C, 62.89; H, 6.50; N, 11.28. Found: C, 63.22; H, 7.00; N, 11.08.

EXAMPLE 12

(2-Pyridyl)oxamic acid sec-butyl ester. 100

2-Aminopyridine is condensed with secondary butyl oxalyl chloride in a manner similar to the procedure of example 3 to afford the title compound as a liquid, b.p. 112°–116° C./0.05 mm Hg.

Elemental Analysis for $C_{11}H_{14}N_2O_3$: Calc'd: C, 59.45; H, 6.35; N, 12.60. Found: C, 59.48; H, 6.62; N, 12.60.

EXAMPLE 13

Oxanilic acid ethyl ester. 100/64

The title compound is known in the literature: G. Tiere, Rec. Trav. Chim., 52, 420–4 (1933). It is crystallized from ethanol, m.p. 64°–67° C.

EXAMPLE 14

Oxanilic acid methyl ester. 100/52

The title compound is known in the literature: Heilbron Dict. of Org. Cpds., IV, p. 32. (1965). It is crystallized from diethyl ether, m.p. 113°–116° C.

EXAMPLE 15

Oxanilic acid n-propyl ester. 82

The title compound is known in the literature: Heilbron Dict. of Org. Cpds., Vol. IV, p. 32, (1965). It is crystallized from diethyl ether, m.p. 90°–92° C.

EXAMPLE 16

Oxanilic acid i-propyl ester. 100/60

The title compound is known in the literature: Heilbron Dict. of Org. Cpds., Vol, IV, p. 32 (1965) It is crystallized from pentane, m.p. 51°–53° C.

EXAMPLE 17

Oxanilic acid phenyl ester. 59

The title compound is known in the literature; R. Stolle et.al., Ber. Deut. Chem., 54B, 1213–20 (1921). It is crystallized from ethanol, m.p. 136°–139° C.

EXAMPLE 18

1H-Tetrazole-5-carboxanilide. 100/100

The title compound is known in the literature: B. E. Fisher, et.al., J. Org. Chem., 24, 1650 (1959). It is crystallized from ethanol-water, m.p. 216°–218° C. (dec.).

EXAMPLE 19

2'-Carboxyoxanilic acid 1-ethyl ester. 50

The title compound is known in the literature: J.A.C.S. 32, 119 (1910). It is crystallized from toluene, m.p. 182°–183° C.

EXAMPLE 20

2'-Carbamoyloxanilic acid ethyl ester. 90

The title compound is known in the literature: B. R. Baker et.al., J. Org. Chem., 27, 4672 (1962). It is crystallized from ethanol, m.p. 160°–161° C.

EXAMPLE 21

2'-Cyanooxanilic acid ethyl ester. 53

2'-Carbamoyloxanilic acid ethyl ester (5 g, 0.021 mole) is refluxed in 50 ml of acetic anhydride for 2 hrs. The solvent is removed on a rotary evaporator and the residue is slurried in water and diethyl ether, separated, and the ether layer is washed with sat. $NaHCO_3$, brine and dried with $Na_2SO_4$. Evaporation of the ether gives 5 g of a residue which is chromatographed on 150 g silica gel with benzene. Elution with 10 percent diethyl ether in benzene removes 0.68 g of the title compound, m.p. 90°–91° C. after crystallization from ethanol.

Elemental Analysis for $C_{11}H_{10}N_2O_3$: Calc'd: C, 60.54; H, 4.62; N, 12.84. Found: C, 60.36; H, 4.50; N, 12.67.

EXAMPLE 22

2'-Methyloxanilic acid ethyl ester. 75

The title compound is known in the literature: P. E. Todesco et.al., C.A. 61:419f. It is a liquid, b.p. 126° C./0.05 mm. Hg.

EXAMPLE 23

2'-Methoxyoxanilic acid ethyl ester. 100

The title compound is known in the literature: C.A.:61 (4192). It is crystallized from benzene, m.p. 81°–85° C.

EXAMPLE 24

3'-Methoxyoxanilic acid ethyl ester. 38

The title compound is known in the literature: P. A. Petyunin et.al., Zh. Obshch. Khim., 21, 1859–61 (1951). It is crystallized from methanol-water, m.p. 95°–98° C.

EXAMPLE 25

3'-Trifluoromethyloxanilic acid ethyl ester. 64

The title compound is known in the literature: A. Buruffini, et.al., Farmaco, Ed. Sci., 22 (9), 717–34 (1967). It is crystallized from ethanol, m.p. 120°–123° C.

EXAMPLE 26

3'-Fluorooxanilic acid ethyl ester. 78 m-Fluoroaniline (5.55 g, 0.05 mole) is condensed with 6.16 ml (0.055 mole) of ethyl oxalyl chloride in a manner similar to example 3, giving 9.26 g of the title compound, m.p. 85°–89° C. after crystallization from ethanol.

Elemental Analysis for $C_{10}H_{10}FNO_3$: Calc'd: C, 57.0; H, 4.78; N, 6.64. Found: C, 56.45; H, 4.87; N, 6.61.

EXAMPLE 27

3'-Methyloxanilic acid ethyl ester. 85

The title compound is known in the literature: P. A. Petyunin et.al., Zh. Obshch. Khim., 24, 1078–82 (1954). It is crystallized from benzene-hexane, m.p. 56°–60° C.

EXAMPLE 28

4'-Carbamoyloxanilic acid ethyl ester. 55 p-Aminobenzamide (4.08 g, 0.03 mole) is condensed with 3.7 ml (0.033 mole) of ethyl oxalyl chloride in a manner similar to example 3, giving 2.85 g of the title compound, m.p. 259°–264° C. (dec.), after crystallization from N,N-fdimethylformamide.

Elemental Analysis for $C_{11}H_{12}N_2O_4$: Calc'd: C, 55.93; H, 5.12; N, 11.86. Found: C, 56.01; H, 5.24; N, 11.92.

EXAMPLE 29

4'-Methoxyoxanilic acid ethyl ester. 75/76

The title compound is known in the literature: A. Piutti et.al., Br. Deut. Chem., 31, 330–336 (1898). It is crystallized from ethanol, m.p. 100°–104° C.

EXAMPLE 30

4'-Nitrooxanilic acid ethyl ester. 75

The title compound is known in the literature: G. Tierie, Rec. Trav. Chim., 52, 420–4 (1933). It is crystallized from acetic acid, m.p. 169°–172° C.

EXAMPLE 31

4'-Methyloxanilic acid ethyl ester. 100

The title compound is known in the literature: C.A. 61 (4192g). It is crystallized from benzene-hexane, m.p. 65°–67° C.

EXAMPLE 32

4'-Phenylazooxanilic acid ethyl ester. 41 p-Phenylazoaniline (5.92 g, 0.03 mole) is condensed with 3.7 ml (0.033 mole) of ethyl oxalyl chloride in a manner similar to example 3, giving 7.36 g of the title compound, m.p. 157°–160° C., after crystallization from ethanol.

Elemental Analysis for $C_{16}H_{15}N_3O_3$: Calc'd: C, 64.63; H, 5.09; N, 14.14. Found: C, 64.61; H, 5.13; N, 14.04.

EXAMPLE 33 p-Phenylenebisoxamic acid diethyl ester. 77

The title compound is known in the literature: C.A. 60 (P3012b). It is crystallized from ethanol, m.p. 214°–217° C.

EXAMPLE 34

2'-Carbamoyl-3'-methoxyoxanilic acid ethyl ester. 100/94

6-Amino-o-anisamide (8.75 g, 0.0527 mole) is condensed with 6.2 ml (0.0554 mole) of ethyl oxalyl chloride in a manner similar to example 3, giving 8.35 g of the title compound, m.p. 170°–173° C., after crystallization from ethanol.

Elemental Analysis for $C_{12}H_{14}N_2O_5$: Calc'd: C, 54.13; H, 5.30; N, 10.52. Found: C, 54.36; H, 5.20; N, 10.66.

EXAMPLE 35

2-Carboxy-3'-methoxyoxanilic acid ethyl ester. 54

6-Amino-o-anisic acid (1.671 g, 0.01 mole) is condensed with 1.23 ml (0.011 mole) of ethyl oxalyl chloride in a manner similar to example 3, giving 1 g of the title compound, m.p. 142°–144° C., after crystallization from ethanol.

Elemental Analaysis for $C_{12}H_{13}NO_6$: Calc'd: C, 53.93; H, 4.90; N, 5.24. Found: C, 54.21; H, 4.99; N, 5.32.

EXAMPLE 36

2'-Cyano-3'-methoxyoxanilic acid ethyl ester. 80/71

2-Amino-6-methoxybenzonitrile (4.67 g, 0.0315 mole) is condensed with 3.88 ml (0.0346 mole) of ethyl oxalyl chloride in a manner similar to example 3, giving 5.0 g of the title compound, m.p. 142°–145° C., after crystallization from toluene.

Elemental Analysis for $C_{12}H_{12}N_2O_4$: Calc'd: C, 58.06; H, 4.87; N, 11.29. Found: C, 58.21; H, 4.93; N, 11.02.

EXAMPLE 37

2'-Carbamoyl-3'-chlorooxanilic acid ethyl ester. 25

2-Amino-6-chlorobenzamide (4.26 g, 0.025 mole) is condensed with 3.1 ml (0.0275 mole) of ethyl oxalyl chloride in a manner similar to example 3, giving 5.28 g of the title compound, m.p. 190°–193° C., after crystallization from ethanol.

Elemental Analysis for $C_{11}H_{11}ClN_2O_4$: Calc'd: C, 48.8; H, 4.10; N, 10.35. Found: C, 49.08; H, 4.05; N, 10.72.

EXAMPLE 38

2'-Carboxy-3'-methoxyanilic acid 1-ethyl 2'-methyl ester. 78

Methyl 6-methoxyanthranilic acid (3.62 g, 0.02 mole) is condensed with 2.46 ml (0.022 mole) of ethyl oxalyl chloride in a manner similar to example 3, giving 3.51 g of the title compound, m.p. 96°–99° C. after crystallization from ethanol.

Elemental Analaysis for $C_{13}H_{15}NO_6$: Calc'd: C, 55.51; H, 5.38; N, 4.98. Found: C, 55.56; H, 5.43; N, 5.18.

EXAMPLE 39

2'-Carbamoyl-3'-(2-phenoxyethoxy)oxanilic acid ethyl ester. 75

2-Phenoxyethanol (4.15 ml, 0.033 mole) is added to dimethylsulfoxyl sodium prepared from 1.39 g of 57 percent sodium hydride and 40 ml dimethylsulfoxide, giving a mixture of the solid salt of the alcohol after about 20 minutes. This mixture is added to a solution of 5.8 g (0.030 mole) 2,6-dinitrobenzonitrile in 20 ml of dimethylsulfoxide at 30°–40° C., and the resulting purple solution is stirred over night at room temperature. The solvent is removed at 70° C. on a rotary evaporator, and the residue is triturated with water. A solid is filtered off and it is dissolved in ethylacetate. The ethylacetate solution is washed twice with H₂O, brine, and dried with calcium sulfate. Evaporation of the ethylacetate, gives 8.5 g of 2-nitro-6(2-phenoxyethoxy)benzonitrile, which is crystallized from 200 ml ethyl alcohol, giving 6 g, m.p. 129°–137.5° C.

The crystallized 2-nitro-6-(2-phenoxyethoxy)benzonitrile (5.82 g, 0.0205 mole) is stirred in 116 ml absolute ethanol at 50° C. and 3.62 ml. (0.0615 mole) 85 percent hydrazine hydrate is added, followed by small scoops of Raney nickel. The temperature is kept at 50°–60° C. while the Raney nickel is added, and after gas evolution and the exotherm ceases, the mixture is filtered through diatomaceous earth. The filter cake is washed with hot ethanol and the filtrate is concentrated, giving 2.804 g of 2-amino-6-(2-phenoxyethoxy)-benzamide m.p. 127°–130° C.

Elemental Analysis for $C_{15}H_{16}N_2O_3$: Calc'd: C, 66.16; H, 5.92; N, 10.29. Found: C, 66.71; H, 6.36; N, 10.13.

2-Amino-6-(2-phenoxyethoxy)benzamide (2.8 g, 0.0103 mole) is condensed with 1.26 ml (0.0113 mole) of ethyl oxalyl chloride in a manner similar to example 2, giving 1.62 g of the title compound, m.p. 142°–145° C., after crystallization from ethanol.

Elemental Analysis for $C_{19}H_{20}N_2O_6$: Calc'd: C, 61.28; H, 5.41; N, 7.52. Found: C, 61.14; H, 5.57; N, 7.50.

EXAMPLE 40

2'-Carbamoyl-3'-methoxyoxanilic acid methyl ester. 96

6-Amino-o-anisamide (4.98 g, 0.03 mole) is condensed with 3.04 ml. (0.033 mole) of methyl oxalyl chloride in a manner similar to example 3, giving 4.24 g of the title compound, m.p. 195°–198° C., after crystallization from methanol.

Elemental Analysis for $C_{11}H_{12}N_2O_5$: Calc'd: C, 52.38; H, 4.80; N, 11.11. Found: C, 52.30; H, 4.94; H, 11.40.

EXAMPLE 41

2'-Carbamoyl-3'-methoxyoxanilic acid n-propyl ester. 96

6-Amino-o-anisamide (4.98 g, 0.03 mole) is condensed with 4.25 ml (0.033 mole) of n-propyl oxalyl chloride in a manner similar to example 3, giving 4.81 g of the title compound, m.p. 158°–161° C., after crystallization from acetonitrile.

Elemental Analysis for $C_{13}H_{16}N_2O_5$: Calc'd: C, 55.71; H, 5.75; N, 10.00. Found: C, 55.92; H, 5.93; N, 10.34.

EXAMPLE 42

2'-Carbamoyl-3'-methoxyoxanilic acid isopropyl ester. 57

6-Amino-o-anisamide (4.98 g, 0.03 mole) is condensed with 4.25 ml (0.033 mole) of isopropyl oxalyl chloride in a manner similar to example 3, giving 4.74 g of the title compound, m.p. 128°–132° C., after crystallization from benzene.

Elemental Analysis for $C_{13}H_{16}N_2O_5$: Calc'd: C, 55.71; H, 5.75; N, 10.00. Found: C, 55.66; H, 5.93; N, 10.38.

EXAMPLE 43

2'-Carbamoyl-3'-methoxyoxanilic acid. 48

2'-Carbamoyl-3'-methoxyoxanilic acid ethyl ester (1.33 g, 0.005 mole) is stirred in 50 ml water, and 5.0 ml of N NaOH is slowly added, giving a solution. After ½ hour the solution is filtered, and the filtrate is acidified to pH 2 with N HCl, giving 0.71 g of the title compound, m.p. 214°–215° C., after crystallization from ethanol.

Elemental Analysis for $C_{10}H_{10}O_5N_2$: Calc'd: C, 50.42; H, 4.23; N, 11.76. Found: C, 50.60; H, 4.35; N, 11.80.

EXAMPLE 44

N-(2-Carbamoyl-3-methoxyphenyl)oxamide. 26

2'-Carbamoyl-3'-methoxyoxanilic acid ethyl ester (5.0 g, 0.0188 mole) is added to 50 ml of ethanol saturated with ammonia at 0°–5° C., and the mixture is stirred in an ice-bath for 2 hours, then filtered. The cake is washed with ethanol, giving 1.41 g of the title compound, m.p. 252°–255° C., after crystallization from water.

Elemental Analysis for $C_{10}H_{11}N_3O_4$: Calc'd: C, 50.63; H, 4.67; N, 17.72. Found: C, 50.45; H, 4.70; N, 17.65.

EXAMPLE 45

2'-Carboxy-4'-methoxyoxanilic acid ethyl ester. 61

5-Methoxyanthranilic acid (1.67 g, 0.01 mole) is condensed with 1.23 ml (0.011 mole) of ethyl oxalyl chloride in a manner similar to example 3, giving 1.32 g of the title compound, m.p. 238°–243° C., after crystallization from ethanol.

Elemental Analysis for $C_{12}H_{13}NO_6$: Calc'd: C, 53.93; H, 4.90; N, 5.24. Found: C, 53.99; H, 4.93; N, 4.99.

EXAMPLE 46

2'-Carbamoyl-4'-chlorooxanilic acid ethyl ester. 58

2-Amino-5-chlorobenzamide (3.41 g, 0.02 mole) is condensed with 2.46 ml (0.022 mole) of ethyl oxalyl chloride in a manner similar to example 3, giving 4.57 g of the title compound, m.p. 204°–210° C., after crystallization from acetonitrile.

Elemental Analysis for $C_{11}H_{11}ClN_2O_4$: Calc'd: C, 48.8; H, 4.10; N, 10.35; Cl, 13.10. Found: C, 48.65; H, 3.98; N, 10.26; Cl, 12.84.

EXAMPLE 47

2'-Carbamoyl-4'-nitrooxanilic acid ethyl ester. 59

2-Amino-5-nitrobenzamide (5.43 g, 0.03 mole) is condensed with 3.7 ml (0.033 mole) of ethyl oxalyl chloride in a manner similar to example 3, giving 6.54 g of the title compound, m.p. 206°–209° C., after crystallization from ethanol.

Elemental Analysis for $C_{11}H_{11}N_3O_6$: Calc'd: C, 46.98; H, 3.94; N, 14.94. Found: C, 46.68; H, 3.96; N, 15.12.

EXAMPLE 48

4'-Methoxy-2'-nitrooxanilic acid ethyl ester. 84

The title compound is known in the literature: Zh. Obshch. Khim. 1, 2471-7 (1937). It is crystallized from ethanol, m.p. 154°–160° C.

EXAMPLE 49

2'-Nitro-4'-(trifluoromethyl)oxanilic acid ethyl ester. 29

4-Amino-4-nitrobenzotrifluoride (3.21 g, 0.03 mole) is condensed with 3.7 ml (0.033 mole) of ethyl oxalyl chloride in a manner similar to example 3, giving 7.01 g of the title compound, m.p. 124°–126° C., after crystallization from ethanol.

Elemental Analysis for $C_{11}H_9F_3N_2O_5$: Calc'd: C, 43.1; H, 2.96; N, 9.16. Found: C, 42.97; H, 3.02; N, 9.28.

EXAMPLE 50

2'-Carbamoyl-5'-methoxyoxanilic acid ethyl ester. 91

2-Nitro-4-methoxybenzonitrile (12.8 g) is reduced in a manner similar to example 40, giving 9.0 g of 2-amino-p-anisamide, m.p. 152°–156° C., after crystallization from water.

Elemental Analysis for $C_8H_{10}N_2O_2$: Calc'd: C, 57.82; H, 6.07; N, 16.86. Found: C, 58.60; H, 5.76; N, 16.65.

2-Amino-p-anisamide (4.99 g, 0.03 mole) is condensed with 3.68 ml (0.033 mole) of ethyl oxalyl chloride in a manner similar to example 3, giving 3.84 g of the title compound, m.p. 186°–188° C., after crystallization from ethanol.

Elemental Analysis for $C_{12}H_{14}N_2O_5$: Calc'd: C, 54.13; H, 5.34; N, 10.52. Found: C, 54.29; H, 5.50; N, 10.89.

EXAMPLE 51

5'-Chloro-2'-sulfamoyloxanilic acid ethyl ester. 70

2-Amino-4-chlorobenzenesulfonamide (4.13 g, 0.02 mole) is condensed with 2.46 ml (0.022 mole) of ethyl oxalyl chloride in a manner similar to example 3, giving 3.04 g of the title compound, m.p. 183°–187° C., after crystallization from ethanol.

Elemental Analysis for $C_{10}H_{11}ClN_2O_5S$: Calc'd: C, 39.2; H, 3.65; N, 9.14; S, 10.45. Found: C, 38.95; H, 3.65; N, 9.14; S, 10.86.

EXAMPLE 52

2'-Carboxy-4'-methoxyoxanilic acid 1-ethyl 2'-methyl ester. 58

6-Amino-m-anisic acid methyl ester (4.7 g, 0.0283 mole) is condensed with 3.48 ml (0.0311 mole) of ethyl oxalyl chloride in a manner similar to example 3, giving 5.27 g of the title compound, m.p. 129°–133° C., after crystallization from ethanol.

Elemental Analysis for $C_{13}H_{15}NO_6$: Calc'd: C, 55.51; H, 5.38; N, 4.98. Found: C, 55.72; H, 5.38; N, 5.37.

EXAMPLE 53

2',6'-Dichlorooxanilic acid ethyl ester. 100

The title compound is known in the literature: C.A.: 60 (1621a). It is crystallized from diethyl ether, m.p. 128°–130° C.

EXAMPLE 54

4'-Nitro-3'-(trifluoromethyl)oxanilic acid ethyl ester. 100/73

5-Amino-2-nitrobenzotrifluoride (6.18 g, 0.03 mole) is condensed with 3.7 ml (0.033 mole) of ethyl oxalyl chloride in a manner similar to example 3, giving 6.07 g of the title compound, m.p. 106°–110° C., after crystallization from ethanol.

Elemental Analysis for $C_{11}H_9F_3N_2O_5$: Calc'd: C, 43.1; H, 2.96; N, 9.16. Found: C, 43.26; H, 2.95; N, 9.18.

EXAMPLE 55

4,4'-Oxydioxanilic acid diethyl ester. 34

The title compound is known in the literature: CA.: 60 (P 3012b). It is crystallized from ethanol, m.p. 159°–162° C.

EXAMPLE 56

2'-Carbamoyl-3'-methoxyoxanilic acid cyclohexyl ester. 91

6-Amino-o-anisamide is condensed with cyclohexyl oxalyl chloride to afford the title compound, m.p. 166°–169° C. Elemental Analysis: $C_{16}H_{20}N_2O_5$: Calc'd: C, 59.99; H, 6.29; N, 8.75. Found: C, 60.17; H, 6.33; N, 8.69.

EXAMPLE 57

2'-Carbamoyl-3'-methoxyoxanilic acid butyl ester. 98

6-Amino-o-anisamide is condensed with n-butyl oxalyl chloride to afford the title compound, m.p. 126°–129° C.

Elemental Analysis for $C_{14}H_{18}N_2O_5$: Calc'd: C, 57.13; H, 6.17; N, 9.52. Found: C, 57.43; H, 6.46; N, 9.38.

EXAMPLE 58

2'-Carbamoyl-3'-methoxyoxanilic acid sec-butyl ester. 100/70

6-Amino-o-anisamide is condensed with secondary butyl oxalyl chloride to afford the title compound, m.p. 119°–122° C.

Elemental Analysis for $C_{14}H_{18}N_2O_5$: Calc'd: C, 57.13; H, 6.17; N, 9.52. Found: C, 56.94; H, 6.44; N, 9.50.

EXAMPLE 59

2'-Carbamoyl-3'-ethoxyoxanilic acid ethyl ester. 80

2-Amino-6-ethoxy-benzoic acid amide is condensed with ethyl oxalyl chloride to afford the title compound m.p. 142°–145° C.

EXAMPLE 60

2'-Carbamoyl-3'-propoxyoxanilic acid ethyl ester. 52

2-Amino-6-propoxy-benzoic acid amide is condensed with ethyl oxalyl chloride to afford the title compound, m.p. 130°–133° C.

EXAMPLE 61

2'-Carbamoyl-3'-isopropoxyoxanilic acid ethyl ester 60

2-Amino-6-isopropoxy-benzoic acid amide is condensed with ethyloxalyl chloride to afford the title compound, m.p. 123°–125° C.

EXAMPLE 62

2'-Carbamoyl-3'-n-butoxyoxanilic acid ethyl ester. 75

2-Amino-6-n-butoxy-benzoic acid amide is condensed with ethyl oxalyl chloride to afford the title compound, m.p. 120°–123° C.

EXAMPLE 63

(2-Naphthyl)oxamic acid ethyl ester. 76

The title compound is known in the literature: C.A. 43:697 g, m.p. 118°–120° C.

EXAMPLE 64

(1-Naphthyl)oxamic acid ethyl ester. 97

The title compound is known in the literature: C.A. 43:6973 g, m.p. 105°–107° C.

EXAMPLE 65

3', 4', 5'-Trimethoxyoxanilic acid ethyl ester. 63

The title compound is known in the literature: C.A. 68:9547 y, m.p. 132°–134° C.

Elemental Analysis for $C_{13}H_{17}NO_6$: Calculated: C, 55.12; H, 6.05; N, 4.95. Found: C, 55.14; H, 6.26; N, 4.87.

EXAMPLE 66

N-(2-Pyridyl)oxamic acid N'- oxide ethyl ester. 94/51

A solution of 4.07 g. (0.02 mole) of 85% m-chloroperbenzoic acid in 75 ml. of $CHCl_3$ was dropped into a solution of 3.88 g. (0.02 mole) of N-(2-pyridyl) oxamic acid ethyl ester in 50 ml. of $CHCl_3$. After stirring overnight at room temperature, the solution was passed through a column of Grade I Woelm basic alumina followed by 400 ml. of $CHCl_3$. Elution was 800 ml. of 3:1 $CHCl_3/CH_3OH$ gave 1.31 g. after crystallization from ethylacetatehexane: mp. 128°–130° C.

Elemental Analysis for $C_9H_{10}N_2O_4$: Calc'd: C, 50.76; H, 4.67; N, 13.45. Found: C, 51.00; H, 4.67; N, 13.58.

EXAMPLE 67

3'-Methoxy-2'-methylcarbamoyloxanilic acid ethyl ester. 72

Slow addition of 4.98 g. (0.03 mole) of 6-amino-o-anisamide to a mixture of 57% NaH (1.32 g., 0.0315 mole) in 50 ml. dimethylformamide was carried out at room temperature. After the evolution of $H_2$ ceased, the mixture was cooled to 3° C. and 2.06 ml. (0.033 mole) of methyliodide was slowly added at 3°–5° C. The temperature was allowed to go up to room temperature and stir for 2 hours. The mixture was concentrated, the residue extracted into ethylacetate-water, the mixture was basified, and the ethylacetate layer was washed with water, brine and dried. Concentration gave a tan solid that was crystallized (ethanol), giving 0.45 g. (8%) of 6-amino-N-methyl-o-anisamide mp. 186°–189° C.

Elemental Analysis for $C_9H_{12}N_2O_2$: Calc'd: C, 59.98; H, 6.71; N, 15.55. Found: C, 60.42; H, 7.04; N, 15.42.

To a solution of 6-amino-N-methyl-o-anisamide (2.85 g., 0.0158 mole) and 2.54 ml. (0.0314 mole) of pyridine in 100 ml. of $CH_2Cl_2$ at 10° C., is added 1.94 ml. (0.0174 mole) of ethyl oxalyl chloride over 5 minutes. After stirring for 2 hours at room temperature, add diethyl ether and wash with water and cold dilute HCl. An insoluble solid is filtered off and crystallized from ethylacetate-hexane, giving 0.3 g. of the title compound (mp. 119°–121° C.). The original organic layer is washed with water, brine and dried with $Na_2SO_4$. Concentration and crystallization of the residue from ethyl acetate-hexane, gave 0.91 g. of the title material: mp. 119°–121° C.

Elemental Analysis for $C_{13}H_{16}N_2O_5$: Calc'd: C, 55.71; H, 5.75; N, 10.00. Found: C, 55.91; H, 6.00; N, 9.94.

EXAMPLE 68

2'-Carbamoyl-3'-(2-dimethylaminoethoxy)oxanilic acid ethyl ester, hydrochloride. 85

Ethyl oxalyl chloride (0.91 ml., 0.008 mole) is added to 1.81 g. (0.008 mole) of 2-amino-6-dimethylaminoethoxybenzamide at 10° C. in 100 ml. of $CH_2Cl_2$ over a period of 5 minutes. After stirring overnight, the mixture is concentrated to dryness on a rotary evaporater and the residue is triturated with diethyl ether and filtered. The solid is crystallized from methanol, giving 1.89 g. of the title compound: mp. 209°–211° C.

Elemental Analysis for $C_{15}H_{22}ClN_3O_5.0.15H_2O$: Calc'd: C, 49.70; H, 6.2; N, 11.6; Cl, 9.78. Found: C, 49.92; H, 6.66; N, 11.64; Cl, 9.85.

The 2-amino-6-dimethylaminoethoxybenzamide reactant is prepared as follows:

To a solution of 14.06 g. (0.0728 mole) of 2,6-dinitrobenzonitrile in 270 ml. of tetrahydrofuran at 40° C., a solution prepared by adding 1.67 g. (0.0726 mole) of sodium to 30 ml. of 2-dimethylaminoethanol is added over 20 minutes. The solution is refluxed for 3 hours, concentrated to dryness on a rotary evaporator and scrubbed three times with xylene. The residue is filtered with water, and crystallized from benzene-hexane, giving 7.79 g. of 2-(2-dimethylaminoethoxy)-6-nitrobenzonitrile mp. 89°–91° C.

Elemental Analysis for $C_{11}H_{13}N_3O_3$: Calc'd: C, 56.16; H, 5.57; N, 17.86. Found: C, 56.11; H, 5.70; N, 17.51.

To a solution of 7.17 g. (0.0305 mole) of 2-(2-dimethylaminoethoxy)-6-nitrobenzonitrile and 3.85 ml. of 85% hydrazine hydrate in 250 ml. of absolute ethyl alcohol at 40° C. is added small portions of Raney nickel. When the exotherm and evolution of gases ceases, the mixture is filtered and the filtrate concentrated to dryness. The residue is crystallized from ethyl acetatehexane, giving 2.13 g. of 2-amino-6-dimethylaminoethoxybenzamide: m.p. 118°–121° C.

EXAMPLE 69

(6-Methyl-2-pyridyl)oxamic acid ethyl ester. 77/74

To a solution of 5.4 g. (0.05 mole) of 2-amino-6-picoline and 8.05 ml. (0.1 mole) of pyridine in 100 ml. of $CH_2Cl_2$ at 10° C. is added 6.16 ml. (0.055 mole) of ethyl oxalyl chloride over 10 minutes. After stirring for 2 hours at room temperature, the solution is concentrated to dryness on a rotary evaporator. The residue is triturated with water and filtered. Crystallization (diethyl ether) gave 6.90 g.:mp. 61°–63° C.

Elemental Analysis for $C_{10}H_{12}N_2O_3$: Calc'd: C, 57.68; H, 5.81; N, 13.46. Found: C, 58.19; H, 6.08; N, 13.28.

EXAMPLE 70

2-(Ethoxycarbonylcarboxamido)-4,5-dimethylbenzoic acid. 33

To a solution of 4,5-dimethylanthranilic acid (3.30 g., 0.02 mole) and 3.22 ml. (0.04 mole) of pyridine in 50 ml. of tetrahydrofuran at 10° C., is added 2.46 ml. (0.022 mole) of ethyl oxalyl chloride over 5 minutes. The reaction is carried out and worked up in a manner similar to example 69, giving 4.27 g. of the title compound after crystallization (ethanol): mp. 235°–239° C.

Elemental Analysis for: $C_{13}H_{15}NO_5$: Cald'd: C, 58.86; H, 5.70; N, 5.28. Found: C, 59.15; H, 5.73; N, 5.20.

EXAMPLE 71

(2-Carbamoyl-4,5-dimethylphenyl)oxamic acid ethyl ester. 100

Liquid phosgene (55 g.) is added to a stirred solution of 30.1 g. (0.182 mole) of 4,5-dimethylanthranilic acid in 800 ml. of dioxane. The temperature is raised to 40°–45° C. and held for 2 hours, and then stirred overnight at room temperature. The mixture is filtered and the cake washed with diethyl ether, giving 33 g. of the isatoic anhydride: mp.>300° C. The isatoic anhydride is then added to 435 ml of N $NH_4OH$, and the mixture stirred overnight at room temperature. The mixture is refluxed for 2 hours, cool, filter, and crystallize (ethanol), giving 13.4 g. of 2-amino-4,5-dimethylbenzamide: mp. 162°–7° C.

To a solution of 1.99 g. (0.0121 mole) of 2-amino-4,5-dimethylbenzamide and 1.95 ml. (0.0242 mole) of pyridine in 50 ml. of tetrahydrofuran at 10° C. is added 1.49 ml. (0.0133 mole) of ethyl oxalyl chloride over 5 minutes. The reaction is carried out and worked-up in a manner similar to example 69, giving 2.73 g. of the title compound after crystallization (ethanol), mp. 190°–193° C.

Elemental Analysis for $C_{13}H_{16}N_2O_4$: Calc'd: C, 59.08; H, 6.10; N, 10.60. Found: C, 58.82; H, 6.31; N, 10.41.

EXAMPLE 72

2'-Acetyl-3'-methoxyoxanilic acid ethyl ester. 46

To a solution of 2-amino-6-methoxyacetophenone (2.1 g., 0.0127 mole) and 2.05 ml. (0.0254 mole) of pyridine in 50 ml. of methylene chloride at 10° C., is added 1.49 ml. (0.0133 mole) of ethyl oxalyl chloride over 5 minutes. The reaction is carried out and worked-up in a manner similar to example 69, giving 2.06 g. of the title compound after chromatography on acidic silica gel: mp. 70°–73° C.

Elemental Analysis for $C_{13}H_{15}NO_5$: Calc'd: C, 58.86; H, 5.70; N, 5.28. Found: C, 58.89; H, 5.66; N, 5.23.

EXAMPLE 73

2'-Carbamoyl-3'-(2-hydroxypropoxy)oxanilic acid ethyl ester. 100

In a manner similar to example 68, but using 1,2-propanediol instead of 2-dimethylaminoethanol, one isolates a 39% yield of 2-(2-hydroxy propoxy)-6-nitrobenzonitrile after crystallization (benzene): mp. 121°–124° C.

Elemental Analysis for $C_{10}H_{10}N_2O_4$: Calc'd: C, 54.05; H, 4.54; N, 12.61. Found: C, 54.24; H, 4.64; N, 12.67.

2-Amino-6-(2-hydroxypropoxy)benzamide is produced by reducing the benzonitrile in accordance with Example 68, in 78% yield after crystallization (ethylacetate-hexane): mp. 115°–118° C.

Elemental Analysis for $C_{10}H_{14}N_2O_3$: Calc'd: C, 57.13: H, 6.71, N, 13.33. Found: C, 57.55; H, 6.56; N, 13.33.

To a solution of 2-amino-6-(2-hydroxy propoxy)benzamide (2.05 g., 0.00976 mole) and 1.57 ml. (0.01952 mole) of pyridine in 200 ml. of $CH_2Cl_2$ at 10° C., is added 1.09 ml. (0.00976 mole) of ethyl oxalyl chloride over 20 minutes. The reaction is carried out and worked-up in a manner similar to example 69, giving 0.18 g. of the title material after chromatography on acidic silica gel and crystallization (ethyl acetate-hexane): mp. 131°–135° C.

Elemental Analysis for $C_{14}H_{18}N_2O_6$: Calc'd: C, 54.19; H, 5.85; H, 9.03. Found: C, 54,38; H, 6.09; N, 8.97.

EXAMPLE 74

(2-Carbamoyl-3,5-dimethoxyphenyl)oxamic acid ethyl ester. 100/19 at 25 mg/kg

A solution of 1.96 g. (0.01 mole) of 4,6-dimethoxy anthranilamide in 50 ml. of methylenechloride is treated with pyridine and ethyl oxalyl chloride. After 1 hour the reaction mixture is filtered and the crude product is recrystallized from dimethylformamide-ethyl acetate to give 2.4 g. of product, mp. 198°–208° C.

Elemental Analysis for $C_{13}H_{16}N_2O_6$: Calc'd: C, 52.70; H, 5.44; N, 9.46. Found: C, 52.75; H, 5.56; N, 9.54.

4,6-Dimethoxyanthranilamide is prepared as follows:

A mixture of 6.7 g. (0.03 mole) of 4,6-dimethoxy isatoic anhydride and 75 ml. of 1M ammonium hydroxide is stirred 16 hours at room temperature. The solid is filtered off, dried and extracted with hot ethanol. The extracts are cooled and diethyl ether is added to give a first crop 1.2 g., mp. 198°–200° C. followed by a second crop of the desired amide, mp. 117°–119° C., 2.3 g.

Elemental Analysis for $C_9H_{12}N_2O_3$: Calc'd: C, 55.09; H, 6.17; N, 14.28. Found: C, 55.01; H, 6.21; N, 14.12.

4,6-Dimethoxyisatoic anhydride is prepared from 4,6-dimethoxyanthranilic acid (H. Newman & R. Anzier, J. Org. Chem. 34, 3484 (1969)) and phosgene according to the method of E. C. Wagner and M. F. Fegley, Org. Synthesis 27, 45 (1947).

EXAMPLE 75

Oxalic acid (2-[2-aminocarbonyl-3-ethoxy carbonylcarbonylamino phenoxy]ethyl)ethyl ester. 82/26 at 10 mg/kg.

2-Amino-6-(2-hydroxyethoxy)benzamide is treated with two equivalents of pyridine and ethyl oxalyl chloride. The usual workup gives a white solid which is triturated with hot ethanol and filtered to give the product, mp. 180°–182° C.

Elemental Analysis for $C_{17}H_{20}N_2O_9$: Calc'd: C, 51.51; H, 5.09; N, 7.07. Found: C, 51.39; H, 5.00; N, 7.11.

2-Amino-6-(2-hydroxyethoxy)benzamide is prepared by the following procedure:

A suspension of 6.0 g. of 2-(2-hydroxyethoxy)-6-nitrobenzonitrile on 30 ml. of ethanol and 4.3 ml. of hydrazine hydrate is added slowly to a suspension of 2.9 g. of Raney nickel in 50 ml. of ethanol at such a rate to keep the temperature at 65° C. The mixture is heated to reflux for ½ hour after the addition is complete, filtered through Celite and evaporated to dryness. The solid is recrystallized from ethanol to give 5.3 g. (94%) of amide, mp. 149°–151° C.

Elemental Analysis for $C_9H_{12}N_2O_3$: Calc'd: C, 55.09; H, 6.17; N, 14.28. Found: C, 54.84; H, 6.17; N, 14.27.

The 2-(2-hydroxyethoxy)-6-nitrobenzonitrile is prepared as follows:

To a solution of 19.3 g. of 2,6-dinitrobenzonitrile in 500 ml. in tetrahydrofuran at reflux is added dropwise a solution of lithium hydroxyethoxide in tetrahydrofuran prepared by adding 62.5 ml. of 1.6 M butyllithium in hexane to a solution of 6.2 g. of ethylene glycol in 100 ml. of tetrahydrofuran at −78° C. and stirring for 1 hour. After all the ethoxide is added the reaction mixture is refluxed for 4 hours, cooled and evaporated to dryness. The resulting solid is extracted with hot benzene which yields 8.5 g. of product on cooling, mp. 140°–142° C.

Elemental Analysis for $C_9H_8N_2O_4$: Calc'd: C, 51.92; H, 3.87; N, 13.46. Found: C, 51.98; H, 3.92; N, 13.54.

EXAMPLE 76

[2-Carbamoyl-3-(2-hydroxyethoxy)phenyl]oxamic acid ethyl ester 12 at 10 mg/kg per os; 49 at 30 mg/kg per os; 43 at 100 mg/kg per os.

To a suspension of 5.8 g. (30 mmole) of 2-amino-6-(2-hydroxyethoxy)benzamide in 100 ml. of dichloromethane is added 9.48 g. (120 mmole) of pyridine followed by 6.48 g. (60 mmole) of trimethylchlorosilane. After stirring 1 hour, 4.01 g. (30 mmole) of ethyl oxalyl chloride is added. The resulting solution is stirred for 48 hours, poured into dilute hydrochloric acid and the organic phase is separated. The aqueous layer is extracted with methylene chloride, the combined organic layers are washed with dilute hydrochloric acid and dried and evaporated. The residue is recrystallized from ethyl acetate-hexane to give 7.7 g. of product, mp. 146°–148° C.

Elemental Analysis for $C_{13}H_{16}N_2O_6$: Calc'd: C, 52.70; H, 5.44; N, 9.46. Found: C, 52.52; H, 5.42; N, 9.34.

EXAMPLE 77

3-Benzyloxy-2-carbamoylphenyl)oxamic acid ethyl ester.55/22 at 25 mg/kg

2-Amino-6-benzyloxybenzamide is treated with ethyl oxalyl chloride in the usual manner to give the ester, mp. 151°-153° C.

Elemental Analysis for $C_{18}H_{18}N_2O_5$: Calc'd: C, 63.15; H, 5.30; N, 8.18. Found: C, 63.31; H, 5.47; N, 8.36.

2-Amino-6-benzyloxybenzamide is prepared by the Raney nickel reduction of 2-benzyloxy-6-nitrobenzonitrile (E. Cortes & F. Walls, Boll Inst. Quim. Univ. Nach. Auton. Mex. 16, 71(1964); C.A. 63, 533c(1965) in the usual manner; m.p. 158°-160° C.

Elemental Analaysis for $C_{14}H_{14}N_2O_2$: Calc'd: C, 69.40; H, 5.83; N, 11.56. Found: C, 69.25; H, 6.10; N, 11.69.

EXAMPLE 78

N-Hydroxy-N'-phenyloxamide. 92

The title compound is prepared by the method of Dimroth et al., Chem. Ber. 39, 3917; m.p. 165°-167° C.

Elemental Analysis for $C_8H_8N_2O_3$: Calc'd: C, 53.33; H, 4.48; N, 15.55. Found: C, 53.30; H, 4.48; N, 15.07.

EXAMPLE 79

(4-Chlorophenyl)oxamic acid ethyl ester. 64

The title compound was prepared by the method disclosed in Farmaco, Ed. Sci. 22(9), 717-734 (1967); m.p. 149°-152° C.

Elemental analysis for $C_{10}H_{10}NO_3Cl$: Calc'd: C, 52.76; H, 4.43; N, 6.15. Found: C, 52.71; H, 4.40; N, 6.19.

EXAMPLE 80

(4-Dimethylaminophenyl)oxamic acid ethyl ester. 100/16 at 25 mg/kg per os.

The title compound was prepared by the method disclosed in Chem. Abstr., 72, P. 12413 M (1970); m.p. 166°-170° C.

Elemental analysis for $C_{12}H_{16}N_2O_3 \cdot HCl$: Calc'd: C, 52.84; H, 6.28; N, 10.27; Cl, 13.00. Found: C, 52.93; H, 6.28; N, 10.27; Cl, 11.98.

EXAMPLE 81

(3-Cyano-2-pyridyl)oxamic acid ethyl ester. 100

To a solution of 5.95 g. (0.05 mole) of 2-aminonicotinonitrile (E. C. Taylor & A. J. Crovetti, J. Org. Chem. 19, 1633(1954) is 150 ml. of methylenechloride and 7.9g. (0.1 mole) of pyridine is slowly added 6.8 g. (0.05 mole) of ethyloxalyl chloride. After the addition the reaction is stirred for one hour, evaporated to dryness and 5 ml. of water is added. The mixture is filtered and the crude product is recrystallized from methylene chloride-diethyl ether to yield 2.9 g. of pure product, m.p. 95°-97° C.

Elemental Analysis for $C_{10}H_9N_3O_3$: Calc'd: C, 54.79; H, 4.14; N, 19.17. Found: C, 54.59; H, 4.05; N, 18.89.

EXAMPLE 82

[2-(Aminocarbonyl)-3-(dimethylamino)phenyl]oxamic acid ethyl ester. 54/21 at 25 mg/kg per os.

This is prepared from 2-amino-6-dimethylaminobenzamide and ethyl oxalyl chloride in the usual manner, m.p. 133°-135° C.

Elemental analysis for $C_{13}H_{17}N_3O_4$: Calc'd: C, 55.90; H, 6.14; N, 15.05. Found: C, 56.04; H, 6.21; N, 14.54.

2-Amino-6-dimethylamino benzamide is prepared by the Raney nickel reduction of 2-dimethylamino-6-nitrobenzonitrile following the procedure presented in Example 77.

2-Dimethylamino-6-nitrobenzonitrile is prepared from molar equivalents of 2,6-dinitrobenzonitrile and dimethylamine hydrochloride in dimethylformamide in the presence of aqueous KOH.

EXAMPLE 83

[2-Carbamoyl-3-(methylthio)phenyl]oxamic acid ethyl ester. 98/25 at 25 mg/kg per os.

This is prepared by ethyloxalation of 2-amino-6(methylthio) benzamide, m.p. 168°-170° C.

Elemental Analysis for $C_{12}H_{14}N_2O_4S$: Calc'd: C, 51.05; H, 5.00; N, 9.92; S, 11.36. Found: C, 51.06; H, 4.92; N, 10.08; S, 11.65.

2-Amino-6-(methylthio) benzamide is prepared by Raney nickel reduction of 2-(methylthio)-6-nitrobenzonitrile which is prepared from 2,6-dinitrobenzonitrile and methylmercaptan following the procedure set forth in Example 75.

EXAMPLE 84

[(2-Aminocarbonyl-3-methylsulfinylphenyl)amino]oxoacetic acid ethyl ester 44/23 at 25 mg/kg per os A mixture of 2.0 g. of [2-carbamoyl-3-(methylthio)phenyl] oxamic acid ethyl ester and 1.44 g. of m-chloroperoxybenzoic acid in 200 ml. of methylene chloride is stirred for 2 hours. 0.6 g. of sodium bicarbonate in 20 ml. of water is added, the methylene chloride layer is separated, dried and evaporated. The residue is recrystallized from ethanol-diethyl ether, m.p. 164°-166° C.

Elemental Analysis for $C_{12}H_{14}N_2O_5S$: Calc'd: C, 48.31; H, 4.73; N, 9.39; S, 10.74. Found: C, 48.15; H, 4.56; N, 9.26; S, 10.38.

What is claimed is:

1. A compound of the formula:

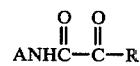

in which

R is a member selected from the group consisting of lower alkoxy, cyclohexyloxy and phenoxy; and

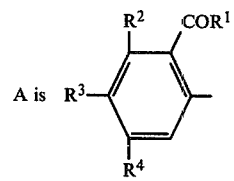

wherein $R^1$ is a member selected from the group consisting of hydroxyl, lower alkyl, lower alkoxy, lower alkylamino and amino radicals;

$R^2$ is a member selected from the group consisting of hydrogen, lower alkoxy, hydroxy(lower)alkoxy, N-mono and di- lower alkylamino(lower)alkoxy, halo, phenoxy(lower)alkoxy, 2-(lower alkoxy oxalyloxy)ethoxy, benzyloxy, mono- and di- lower alkylamino with the proviso that when $R^2$ is hydrogen $R^1$ is other than hydroxyl or lower alkoxy;

$R^3$ is a member selected from the group consisting of hydrogen, lower alkyl, lower alkoxy, halo and nitro; and $R^4$ is a member selected from the group consisting of hydrogen, lower alkyl and lower alkoxy; with the proviso that one of $R^2$, $R^3$ and $R^4$ must be other than hydrogen.

2. A compound of the formula:

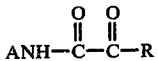

wherein
R is lower alkoxy;

A is 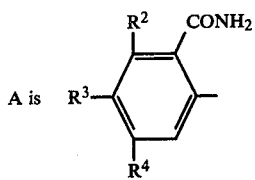

wherein $R^2$ is a member selected from the group consisting of hydrogen, lower alkoxy, di(lower)alkylamino(lower)alkoxy, hydroxy(lower)alkoxy, phenoxy(lower)alkoxy and 2-(lower alkoxy oxalyloxy)ethoxy radicals;

$R^3$ is a member selected from the group consisting of hydrogen, lower alkyl, and lower alkoxy radicals;

$R^4$ is a member selected from the group consisting of —H, lower alkyl and lower alkoxy, with the proviso that one of $R^2$, $R^3$ and $R^4$ must be other than hydrogen.

3. The compound of claim 2 which is 2'-carbamoyl-3'-methoxyoxanilic acid ethyl ester.

4. The compound of claim 1 which is 2'-carboxy-3'-methoxyoxanilic acid ethyl ester.

5. The compound of claim 1 which is 2'-carbamoyl-3'-chlorooxanilic acid ethyl ester.

6. The compound of claim 1 which is 2'-carboxy-3'-methoxyoxanilic acid 1-ethyl 2'-methyl ester.

7. The compound of claim 2 which is 2'-carbamoyl-3'-(2-phenoxyethoxy)oxanilic acid ethyl ester.

8. The compound of claim 2 which is 2'-carbamoyl-3'-methoxyoxanilic acid methyl ester.

9. The compound of claim 2 which is 2'-carbamoyl-3'-methoxyoxanilic acid n-propyl ester.

10. The compound of claim 2 which is 2'-carbamoyl-3'-methoxyoxanilic acid isopropyl ester.

11. The compound of claim 2 which is 2'-carbamoyl-4'-chlorooxanilic acid ethyl ester.

12. The compound of claim 2 which is 2'-carbamoyl-4'-nitrooxanilic acid ethyl ester.

13. The compound of claim 2 which is 2'-carbamoyl-5'-methoxyoxanilic acid ethyl ester.

14. The compound of claim 1 which is 2'-carbamoyl-3'-methoxyoxanilic acid cyclohexyl ester.

15. The compound of claim 2 which is 2'-carbamoyl-3'-methoxyoxanilic acid butyl ester.

16. The compound of claim 2 which is 2'-carbamoyl-3'-methoxyoxanilic acid sec-butyl ester.

17. The compound of claim 2 which is 2'-carbamoyl-3'-ethoxyoxanilic acid ethyl ester.

18. The compound of claim 2 which is 2'-carbamoyl-3'-propoxyoxanilic acid ethyl ester.

19. The compound of claim 2 which is 2'-carbamoyl-3'-isopropoxyoxanilic acid ethyl ester.

20. The compound of claim 2 which is 2'-carbamoyl-3'-n-butoxyoxanilic acid ethyl ester.

21. The compound of claim 1 which is 3'-methoxy-2'-methylcarbamoyloxanilic acid ethyl ester.

22. The compound of claim 2 which is 2'-carbamoyl-3'-(2-dimethylaminoethoxy)oxanilic acid ethyl ester, hydrochloride.

23. The compound of claim 1 which is 2-(ethoxycarbonylcarboxamido)-4,5-dimethylbenzoic acid.

24. The compound of claim 1 which is (2-carbamoyl-4,5-dimethylphenyl)oxamic acid ethyl ester.

25. The compound of claim 2 which is 2'-Acetyl-3'-methoxyoxanilic acid ethyl ester.

26. The compound of claim 2 which is 2'-carbamoyl-3'-(2-hydroxypropoxy)oxanilic acid ethyl ester.

27. The compound of claim 2 which is (2-carbamoyl-3,5-dimethoxyphenyl)oxamic acid ethyl ester.

28. The compound of claim 2 which is oxalic acid (2-[2-aminocarbonyl-3-ethoxy carbonylcarbonylaminophenoxy]ethyl)ethyl ester.

29. The compound of claim 2 which is [2-carbamoyl-3-(2-hydroxyethoxy)phenyl]oxamic acid ethyl ester.

30. The compound of claim 1 which is 3-benzyloxy-2-carbamoylphenyl)oxamic acid ethyl ester.

31. The compound of claim 1 which is [2-(aminocarbonyl)-3-(dimethylamino)phenyl]oxamic acid ethyl ester.

* * * * *